US008979728B2

(12) United States Patent
Zilbershlag (10) Patent No.: US 8,979,728 B2
(45) Date of Patent: Mar. 17, 2015

(54) SAFE ENERGY TRANSFER (75) Inventor: Michael Zilbershlag, Givat Shmuel (IL)

(73) Assignee: Leviticus Cardio Ltd., Givat Shmuel (IL)

( * ) Notice: Subject to any disclaimer, the term of this patent is extended or adjusted under 35 U.S.C. 154(b) by 0 days.

(21) Appl. No.: 13/591,425

(22) Filed: Aug. 22, 2012

(65) Prior Publication Data

US 2013/0053624 A1 Feb. 28, 2013

Related U.S. Application Data (60) Provisional application No. 61/525,932, filed on Aug. 22, 2011.

(51) Int. Cl.
| | | |
|---|---|---|
| *A61M 1/12* | (2006.01) | |
| *A61N 1/378* | (2006.01) | |
| *H01F 7/02* | (2006.01) | |
| *H01F 38/14* | (2006.01) | |

(52) U.S. Cl.
CPC .............. *A61M 1/127* (2013.01); *A61N 1/378* (2013.01); *A61N 1/3787* (2013.01); *A61M 2205/3523* (2013.01); *H01F 7/0247* (2013.01); *H01F 38/14* (2013.01); *A61M 1/122* (2014.02)
USPC ........................................................ 600/16

(58) Field of Classification Search
CPC ...... A61M 1/127; A61N 1/378; A61N 1/3787
USPC .............................................. 607/33, 34, 61
See application file for complete search history.

(56) References Cited

U.S. PATENT DOCUMENTS

| | | | |
|---|---|---|---|
| 4,906,229 A | 3/1990 | Wampler | |
| 4,957,504 A | 9/1990 | Chardack | |
| 5,095,903 A * | 3/1992 | DeBellis | 607/33 |
| 5,507,629 A | 4/1996 | Jarvik | |
| 5,749,855 A | 5/1998 | Reitan | |
| 6,070,103 A * | 5/2000 | Ogden | 607/60 |
| 6,129,704 A | 10/2000 | Forman et al. | |
| 6,135,729 A | 10/2000 | Aber | |
| 6,421,889 B1 | 7/2002 | Chien | |
| 6,527,699 B1 | 3/2003 | Goldowsky | |
| 6,761,681 B2 * | 7/2004 | Schmid et al. | 600/9 |
| 6,772,011 B2 | 8/2004 | Dolgin | |
| 7,613,497 B2 | 11/2009 | Govari et al. | |
| 7,650,192 B2 | 1/2010 | Wahlstrand | |
| 7,741,734 B2 | 6/2010 | Joannopoulos et al. | |
| 7,825,543 B2 | 11/2010 | Karalis et al. | |
| 7,825,776 B2 | 11/2010 | Smith et al. | |
| 7,956,725 B2 | 6/2011 | Smith | |
| 8,075,472 B2 | 12/2011 | Zilbershlag et al. | |
| 8,244,367 B2 | 8/2012 | Wahlstrand et al. | |
| 8,278,784 B2 | 10/2012 | Cook et al. | |
| 8,285,388 B2 | 10/2012 | Wahlstrand | |
| 2004/0014315 A1 | 1/2004 | Lai et al. | |
| 2004/0054251 A1 | 3/2004 | Liotta | |

(Continued)

OTHER PUBLICATIONS

International Search Report for PCT/IL2008/000604 with a date of mailing of Jan. 30, 2009, (4 pages).

*Primary Examiner* — Michael Kahelin (74) *Attorney, Agent, or Firm* — Brown Rudnick LLP (57) ABSTRACT

The invention relates to safety precautions and mechanisms, particularly in connection with a wireless energy transfer system which involves the use of a transmitter (or transceiver) external to a patient's body and also a receiver implanted within a part of the patient's body.

15 Claims, 5 Drawing Sheets

(56) References Cited

U.S. PATENT DOCUMENTS

| | | |
|---|---|---|
| 2004/0115038 A1 | 6/2004 | Nuesser et al. |
| 2005/0220636 A1 | 10/2005 | Henein et al. |
| 2007/0132587 A1 | 6/2007 | Smith et al. |
| 2007/0182578 A1 | 8/2007 | Smith |
| 2008/0041930 A1 | 2/2008 | Smith et al. |
| 2008/0238680 A1 | 10/2008 | Posamentier et al. |
| 2008/0292478 A1 | 11/2008 | Baykut et al. |
| 2009/0243813 A1 | 10/2009 | Smith et al. |
| 2010/0045114 A1 | 2/2010 | Sample et al. |
| 2010/0052811 A1 | 3/2010 | Smith et al. |
| 2010/0076247 A1 | 3/2010 | Zilbershlag et al. |
| 2010/0081379 A1 | 4/2010 | Cooper et al. |
| 2010/0187913 A1 | 7/2010 | Smith et al. |
| 2012/0239118 A1 | 9/2012 | Ozawa et al. |
| 2014/0163307 A1 | 6/2014 | Zilbershlag |

* cited by examiner

SAFE ENERGY TRANSFER

This application claims priority to U.S. Provisional Patent Application No. 61/525,932, filed Aug. 22, 2011, which is incorporated herein by reference in its entirety.

TECHNICAL FIELD

The invention relates to safety precautions and mechanisms, particularly in connection with wireless energy transfer systems.

BACKGROUND INFORMATION

From the earliest days, when Tesla first worked on wireless communication and power transfer, the reliability of a wireless connection has been a source of concern. On the communications side, years of incremental improvement yielded remarkable systems for data transfer (e.g., WIFI) and communication (e.g., cellular phones) but the connections have never been foolproof. As for wireless power transfers, some progress has been made, however, wireless energy transfer has not been widely adopted because of reliability and worries about safety. If wireless energy transfer was safer and more dependable, it would likely be widely accepted. For example, it could be used to power the numerous, battery-dependent, portable devices that consumers have in their home (smart phones, vacuum cleaners, etc.)

If wireless energy transfer were more robust, it could be also be used to power implanted medical devices. Wireless energy transfer to "life-critical" medical devices, such as Ventricular Assist Devices (VAD) would greatly improve the quality of life for patients requiring such devices. Patients having a VAD must constantly wear an external battery pack wired to the device. In addition to the inconvenience of wearing the pack, the wire connecting the battery and the device must be constantly cleaned and monitored to avoid infection. Nonetheless, despite the inconvenience, the use of wireless power for implantable devices—or even wireless communication for such devices—is restricted or avoided in most cases.

One attempt to implement wireless energy transfer for such devices is Transcutaneous Energy Transfer (TET), developed nearly a decade ago. TET uses closely spaced inductive coils, one implanted, and one outside the body, to transfer energy to an implanted rechargeable battery or device. However, just as in the days of Tesla, the technology suffers from concerns about the safety and reliability of the connections used to provide power and communication At the end of the day, a wired connections is far more likely to work than a wireless connection. For this reason, TET, or other implant power schemes, have not been widely adopted.

Some known wireless power transfer approaches are described in U.S. Pat. Nos. 6,772,011, 7,741,734, 7,613,497, 7,825,776, and 7,956,725 and in U.S. Patent Application Publication Nos. 2007-0132587, 2007-0182578, 2008-0041930, 2008-0238680, 2009-0243813, 2010-0045114, 2010-0052811, 2010-0081379, and 2010-0187913.

SUMMARY OF THE INVENTION

In general, the invention relates to safety precautions and mechanisms to be used as a backup when wirelessly transferring power to an internally implanted device. In one example, a transmitter or transceiver that is designed to be placed external to the patient's body can be used to wirelessly send power into the patient's body where that wirelessly-transferred power is then received by an implanted receiver associated with the implanted device. The patient can be a human or an animal, and the part of the body can be the arm, leg, head, or torso of the patient. The device can be an implantable medical device such as a ventricular assist device (VAD), and the received power can be used to operate the pumping action of the VAD. The device can be another type of implantable medical device including, for example, a stent, a glucose meter, a blood-pressure sensing device, a pulse sensing device, a pacemaker, a digital camera, a nerve stimulator, or an ultrasound device. Regardless of the type of implanted device that is coupled to the implanted receiver (and thus powered by the wirelessly-transmitted energy received by the receiver), a safety mechanism can be provided according to the invention to allow for power and/or communication to be supplied to the implanted device in a wired configuration in the event of some emergency situation such as a failure of the wireless transfer of power.

As described herein, the safety mechanism can include a shallowly-implanted female receiving unit disposed just under the skin of the patient at some convenient point on the patient's body such as an area of the chest. The safety mechanism also can include a corresponding external male inserting plug unit that is easily matched and oriented with the under-skin female receiving unit such that one or more extending pins of the male unit can be pushed through the skin and into one or more receiving ports of the female unit. The implanted female unit is electrically connected to the power-requiring implanted device within the patient's body, and the external male unit is electrically connected to a power source external to the patient's body. The skin-puncturing pin(s) of the male unit thus allow a wired connection to be made from the external power source to the implanted device, to provide power to the device in an emergency situation.

Various aspects, features, objects, and advantages of the invention will become apparent through reference to the following description, drawings, and claims. It is noted that aspects of the embodiments described herein are not mutually exclusive and can exist in various combinations and permutations even if not specifically indicated herein.

BRIEF DESCRIPTION OF THE DRAWINGS

In the drawings, like reference characters generally refer to the same or similar parts throughout the different views. The drawings are intended to illustrate the details of one or more embodiments according to the invention and/or the principles of the invention.

As shown in FIG. 1, the system may be coupled to a life-critical implanted device such as a VAD 106 and the accompanying implant controller 107. In some instances, a backup battery 108 is also implanted.

In FIG. 2, external controller 103 provides power to wireless power transceiver 204, an external coil, placed in proximity to an implanted receiver coil 205. The system of FIG. 2 also includes a safety mechanism in the form of an implanted female button 101 and an external male button 102. As shown in FIG. 2, the system may be coupled to a life-critical implanted device such as a VAD 106 and the accompanying implant controller 107. In some instances, a backup battery 108 is also implanted.

FIG. 3 shows the male and female buttons of FIGS. 1 and 2. The implant under the skin unit 301 has female directive inputs 302 and "dummy-proof" measures 303 to validate the correct alignment and direction. The external unit 304 has male pins 305 that use directive holes 306 to make a connection. The external unit also has "dummy-proof" measures 303 to validate the correct alignment and direction during use.

FIG. 4 shows a detailed view of the male buttons of FIG. 3. The external unit 304 has male pins 305 that use directive hole 306. The external unit also has "dummy-proof" measures 303 to validate the correct alignment and direction during use.

FIG. 5 shows a detailed view the female button of FIG. 3. Female button 301 is made of structure 501, and comprises a female connector 502, which includes female directive inputs 302 (other side), which is ultimately connected to an implanted medical device. The implanted unit also has "dummy-proof" measures 503 to validate the correct alignment and direction during use.

FIG. 6 shows a transparent view of the female button of FIG. 5. Structure 501 is designed to receive female connector 502 with a socket 601. Structure 501 also has sockets to receive magnets which provide the "dummy-proof" measures 503.

DESCRIPTION

The invention relates to safety precautions and mechanisms for use when wirelessly transferring power from outside a body of a patient to an internally implanted device. A transmitter or transceiver that is designed to be placed external to the patient's body can be used to wirelessly send power into the patient's body where the wirelessly-transferred power is needed, and received by an implanted receiver associated with the implanted device. The patient can be a human or an animal, and the part of the body can be the arm, leg, head, or torso of the patient. The device can be an implantable medical device such as a ventricular assist device (VAD), and the received power can be used to operate the pumping action of the VAD. The device can be another type of implantable medical device including, for example, a stent, a constant glucose meter (CGM), a blood-pressure sensing device, a pulse sensing device, a pacemaker, a digital camera, a nerve stimulator, or an ultrasound device. Regardless of the type of implanted device that is coupled to the implanted receiver (and thus powered by the wirelessly-transmitted energy received by the receiver), a safety mechanism of the invention can be provided to allow for power to be supplied to the implanted device in a wired configuration in the event of an emergency situation, such as a failure of the wireless transfer of power.

In one embodiment, the safety mechanism includes a shallowly-implanted female receiving unit disposed just under the skin of the patient at some convenient point on the patient's body such as an area of the chest. The safety mechanism also can include a corresponding external male inserting plug unit that is easily matched and oriented with the under-skin female receiving unit such that one or more extending pins of the male unit can be pushed through the skin and into one or more receiving ports of the female unit. Typically, the implanted female unit is electrically connected to the power-consuming implanted device within the patient's body, and the external male unit is electrically connected to a power source external to the patient's body. The skin-puncturing pin(s) of the male unit thus allow a wired connection to be made from the external power source to the implanted device, to provide power to the device in an emergency situation.

Figure 1:
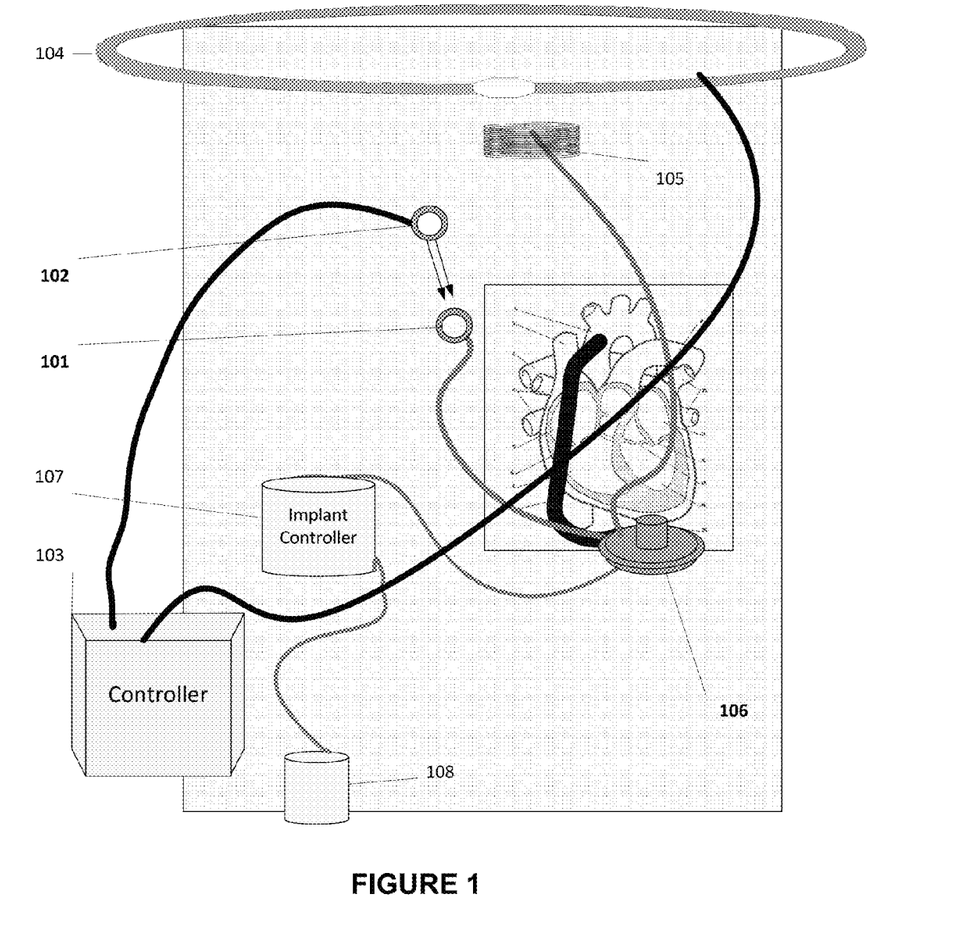
FIG. 1 depicts a coplanar energy transfer (CET) system with an external controller 103 that provides power to wireless power transceiver 104 shown as an external belt surrounding an implanted receiver coil 105. The system includes a safety mechanism in the form of an implanted female button 101 and an external male button 102.

Referring to FIG. 1, the safety device of the invention may be used with a Coplanar Energy Transfer (CET) system, such as described in U.S. patent application Ser. No. 13/588,524, incorporated herein by reference in its entirety. As shown in FIG. 1, when used with a CET, a surrounding belt 104 is coupled with a receiver coil 105 disposed there within. The belt 104 is external to a patient, but the receiver coil 105 is implanted within the patient's body. The implanted receiver coil 105 is electrically connected to an implanted medical device 106, for example a ventricular assist device (VAD), that also is implanted within the patient's body. The receiver coil 105 has one or more turns of electrically-conductive material such as copper, gold, or silver wire, for example. The belt 104 has in or on it, around its entire length, one or more turns of a transmitter coil. Like the receiver coil 105, the transmitter coil can have one or more turns of electrically-conductive material such as copper, silver, or aluminum wire, for example. Together, the external belt 104 with the transmitter coil and the implanted medical device 106 (a VAD in the embodiment shown in FIG. 1) with the connected receiver coil 105, can be considered a wireless power transfer system.

In use, the external belt 104 with the transmitter coil is located externally around the chest of a patient or around some other part of the patient's body such as an arm, a leg, a head, or another part of the patient's torso, and the receiver coil 105 is implanted within that part of the patient's body, such that electromagnetic power inductively transmitted from the surrounding coil of the belt 104 reaches, and is wirelessly received by, the patient-implanted receiver coil 105 from all angles and directions. As also shown in FIG. 1, the CET system typically includes an implanted controller 107 which assists in matching the resonance frequencies between the belt transmitter coil 104 and the receiver coil 105 in order to make the energy transfer more efficient. In some embodiments, a back-up battery unit 108 can be provided within the patient's body. This unit may be a battery, a capacitor, or some other implantable source.

The focus of the instant disclosure is the safe energy transfer system which provides a further safety measure beyond just the patient-implanted back-up battery unit. As shown in FIG. 1, the CET system includes a safety mechanism in the form of an implanted female button 101 and an external male button 102. The implanted female button 101 is electrically connected to the power-requiring implanted device 106 (a VAD, in this example) within the patient's body, and the external male button 102 is electrically connected to the power source (not shown) and external controller 103, both of which are external to the patient's body. In the event of an emergency, the safety buttons 101 and 102 are physically mated together by the patient or someone else. The physical mating of the male and female buttons, 101 and 102, results in a wired electrical connection between the external power source (not shown) and the implanted medical device 106. The wired connection may be used for the transfer of both power and communications between controller 103 and implanted medical device 106.

Figure 2:
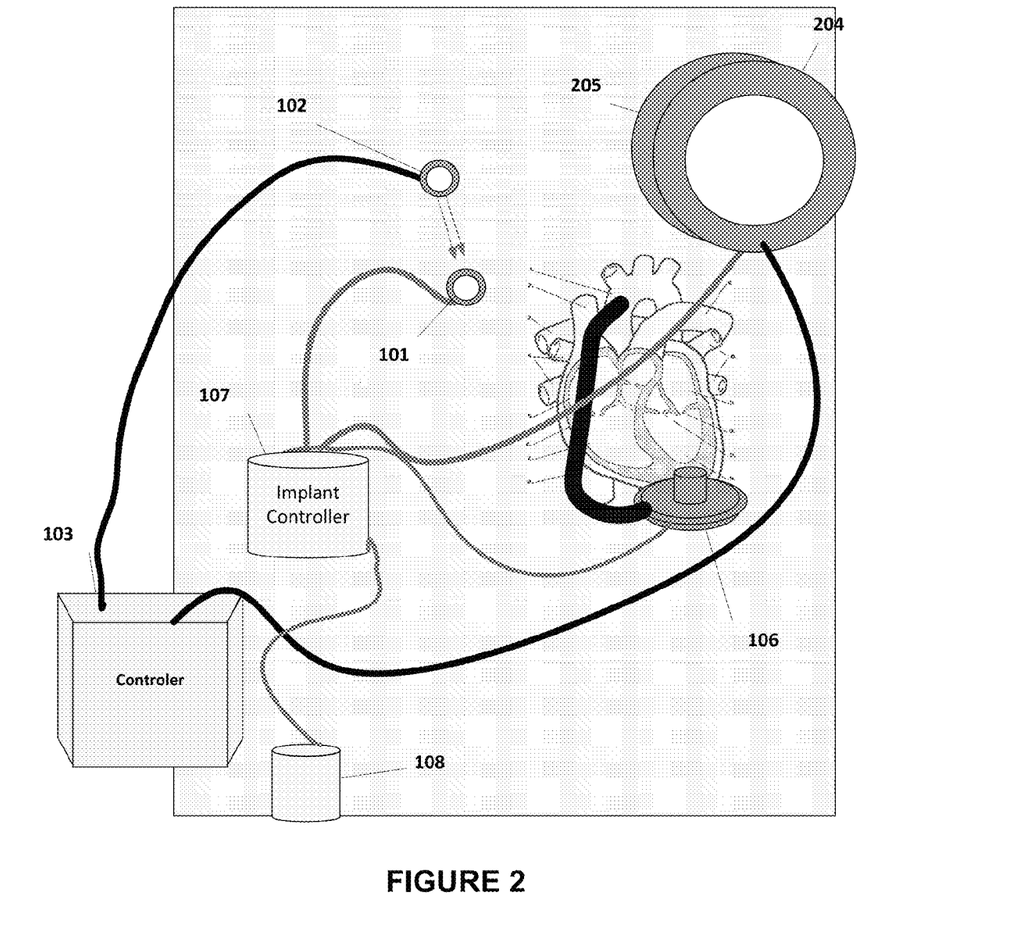
FIG. 2 depicts a conventional transcutaneous energy transfer (TET) system with a safety mechanism like the one shown in FIG. 1.

In alternative embodiments, safety devices of the invention may be used with alternative wireless energy transfer techniques such as Transcutaneous Energy Transfer (TET). The TET system, just as the CET system, is a wireless power transfer system for use with implanted medical devices. As shown in FIG. 2, the wireless power transceiver 204 is an external coil that is located close to an implanted receiver coil 205. A power source (not shown) is electrically connected to the external transmitter coil 204 to provide that coil with the power that it needs to wirelessly transmit energy to the receiving implanted receiver coil 205. The controller unit 103 is also interfaced to the external power source 108. The controller unit 103, in addition to regulating the power to the transmitter coil 204, regulates the operation of the transmitter coil 204. In other embodiments, the external power source also is separate from the external controller. Whether separate from, or part of the controller, an AC current source (not shown) can also be used as the power source.

During normal (non-emergency) use, the external male button 102 typically will be maintained in a sterile sealed pouch or in some other type of protective packaging until it is needed. In the event of an emergency, the external male button 102 will be removed from the pouch such that the patient or someone else can physically mate it to the implanted female button 101 through the skin to provide a wired connection. As discussed previously, the implanted female button 101 will be disposed just under the skin of the patient at some convenient point on the patient's body such as an area of the chest.

The implantation of the female safety button 101 is similar to the subcutaneous implantation of a pacemaker (not shown). In most cases, however, the button 101 is even smaller than a pacemaker, and will require a relatively simple surgery for implantation. In some instances, the safety button 101 will be interfaced to an existing implanted device 106, for example, a VAD. In the instance that another subcutaneous device, (e.g. a pacemaker) is needed to operate the implanted device 106, the subcutaneous device and the safety button 101 may be implanted together. In some instances, the subcutaneous device and the safety button 101 can be incorporated into a single implantable package. In other embodiments that use an implanted back-up battery 108, the safety button 101 may be directly connected to the battery 108. In some embodiments, the safety button 101 will be directly attached to the receiver coil 105.

Figure 3:
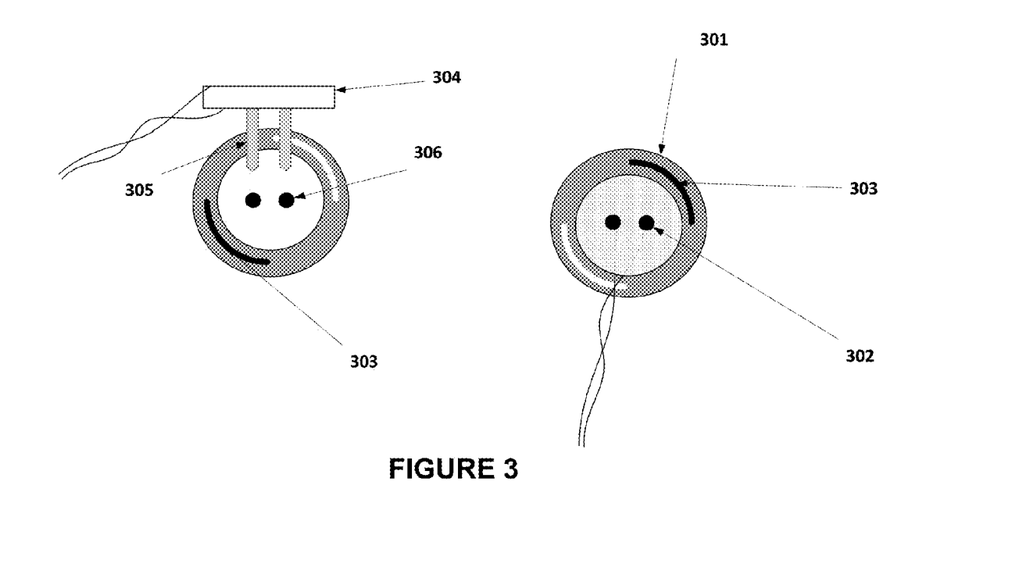

As shown in FIG. 3, the corresponding external male unit 304 is designed to be easily matched and oriented with the under-skin female receiving unit 301, such that one or more extending pins or prongs 305 of the male unit 304 can be pushed through the skin and into one or more receiving ports 302 of the female unit. The skin-puncturing pin(s) 305 of the male unit thus allow a wired connection to be made from the external power source to the implanted device 106, to provide non-wireless power to the device 106 in an emergency situation or any other appropriate situation as determined by the patient or someone else such as a medical professional or medical care provider.

FIG. 3 shows the safety mechanism's external male unit 304 and implantable female unit 301 in greater detail. The male unit 304 is shown having two pins 305, and the female unit 301 is shown with two corresponding receiving ports 302 for accepting the pins 305 of the male unit. A different number of pins 304 and ports 302 is possible such as one, three, four, etc. The pins 305 of the male unit 304, however many there are, are configured to be able to be pushed (by a hand of the patient or someone else attending to the patient) through the skin of the patient and into the receiving ports 302 of the implanted female unit 301. When pushed from the top (non-pin) side of the male button 304 unit, the male unit's pins 305 actually puncture the patient's skin and enter into the below-the-skin ports 302 of the implanted female unit 301. The electrical connection between the male unit 304 and the female unit 301 is made by this physical insertion of the male unit's pins 305 into the female unit's ports 302. The connection may provide power and/or communication between the external controller 103 and the implanted device 106.

The external male unit 304 of the safety mechanism readily matches and orients itself with the under-skin female receiving unit 301 such that the extending pin(s) 305 of the male unit 304 can be pushed through the skin and into the receiving port(s) 302 of the female unit 301 both quickly and confidently by the patient, or whomever is operating the safety mechanism for the patient. One approach to ensuring that any operator of the safety mechanism can quickly and confidently mate the male 304 and female 301 units involves the use of one or more alignment tools, such as magnets. (See also FIGS. 4-6.)

In the magnet-guiding approach, one or more magnets 303 are used in each of the male 304 and female 301 units, and the magnet (or magnets) 303 in each unit has (or have) a different magnet orientation such that an operator will feel when the external male unit 304 is oriented properly for insertion of its pins 305 into the female unit's 301 receiving ports 302 due to the magnetic attraction. If the magnets 303 of the male 304 and female 301 units are not properly oriented, the operator will feel the male unit 304 being repelled by the female unit 301. Thus, a user is assured that prongs 305 will only interface with receiving ports 302 with the correct pin alignment, polarity, etc. Knowledge that the alignment must be correct will allow a patient or user to confidently push prongs 305 through the skin into receiving ports 302, without worry that the prongs will be damaged or mismatched during the process.

Another approach to ensure that any operator of the safety mechanism can quickly and confidently mate the external male pinned unit with the implanted female ported unit is by crafting the male 304 and female 301 units with a mating mechanical shapes. That is, a bulge, asymmetry, or other non-uniform physical aspect of the implanted female unit 301, together with a corresponding reverse physical feature of the external male unit 304, can provide an operator with a clear tactile indication of when the male 304 and female 301 units are properly oriented.

Yet another example of an approach to ensuring that any operator of the safety mechanism can quickly and confidently mate the external male pinned unit with the implanted female ported unit is the use of a tattoo. The skin of the patient immediately above the location where the implanted female unit 301 is disposed within the patient's body can be marked with temporary or permanent ink or other marking material such that an operator can see how to orient and push in the male unit. The male unit 304 may have accompanying visual alignment indicators, such as colored cross-sights, to ensure that the two components mate correctly.

Other male/female unit orientation aids and approaches are possible. For example, the safety mechanism can be designed with electronics that allow the male unit 304 to be inserted into the female unit 301 in either or any orientation. The electronics (part of controller 103) would sense the orientation and alter polarization and/or one or more other parameters to allow the connected male 304 and female 301 units to properly electrically connect and provide the needed wired power connection.

Simple orientation sensing may be achieved with electronics, for example, by adding secure diodes that protect the circuitry from incorrect orientation. Using a simple test current the monitoring circuit will either sense a current/voltage drop (correct orientation), or it will sense zero current, in which case it is necessary to change orientation. At this point, the orientation can be changed electronically using relays, or other measures, or the user would be indicated to alter the orientation of the male unit 304. (It should also be noted that a specific orientation may not be required for mating the male 304 and female 301 units depending on the type of power being delivered and/or the type of communication. For example, AC power delivery may not require a particular orientation between the pins 305 of the male unit and the receiving ports 302 of the female unit, and differential communication also may not require a particular orientation of the male pins 305 and the female ports 302.)

Figure 4:
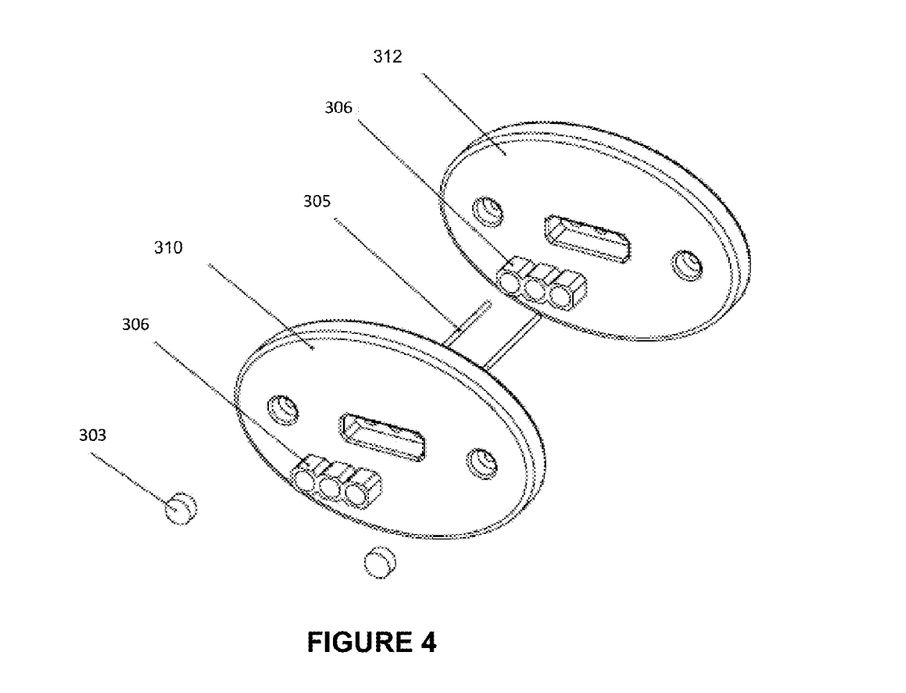
Figure 5:
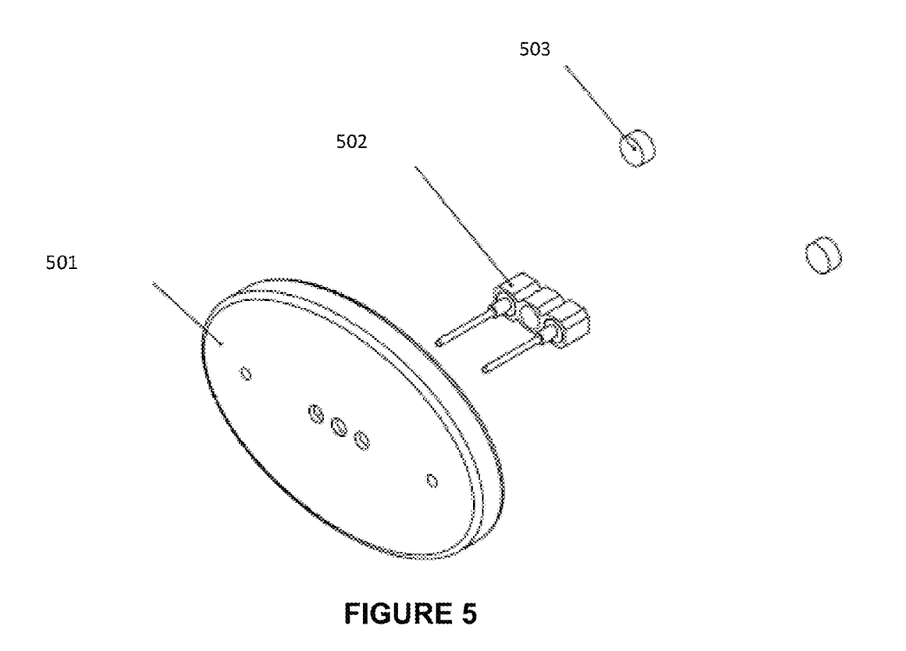
Figure 6:
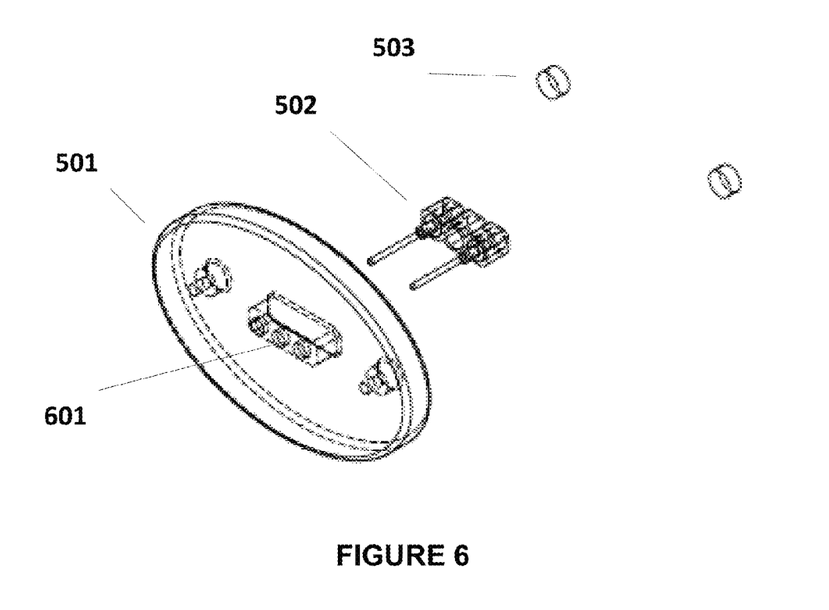

A full schematic example of an embodiment of a safety button design is described in FIGS. 4-6. FIG. 4 describes external male unit 304 in detail. FIGS. 5 and 6 describe female implantable unit 301 in detail.

As shown in FIG. 4, the external unit 304 has male pins 305 that use directive holes 306. The external unit also has "dummy-proof" measures 303, in this case magnets, to validate the correct alignment and direction during use. The male pins 305 will typically be connected to a controller or external power supply. In one embodiment (shown better in FIG. 7) the external male unit comprises two structures 310 and 312 that are aligned to easily pierce the skin in the correct orientation. Thus, first structure 310 is orientated against the skin above female unit 301 in the correct orientation, and then the second structure 312, to which prongs 305 are attached, is pushed against the first structure 310, driving prongs 305 through directive holes 306 and into female ports 302.

FIG. 5 shows details of the female buttons of FIGS. 1-3. Female button 301 is made of structure 501, and comprises a female connector 502, which includes female directive inputs 302 (other side), which is ultimately connected to an implanted medical device. The implanted unit also has "dummy-proof" measures 503 to validate the correct alignment and direction during use. The female connector 502 will receive prongs 305 once pushed through the skin, thereby making a connection between external controller 103 and implanted device 106.

FIG. 6 shows a transparent view of the female button of FIG. 5. Structure 501 is designed to receive female connector 502 with a socket 601. Structure 501 also has sockets to receive magnets 503 which provide the "dummy-proof" measures.

Figure 7:
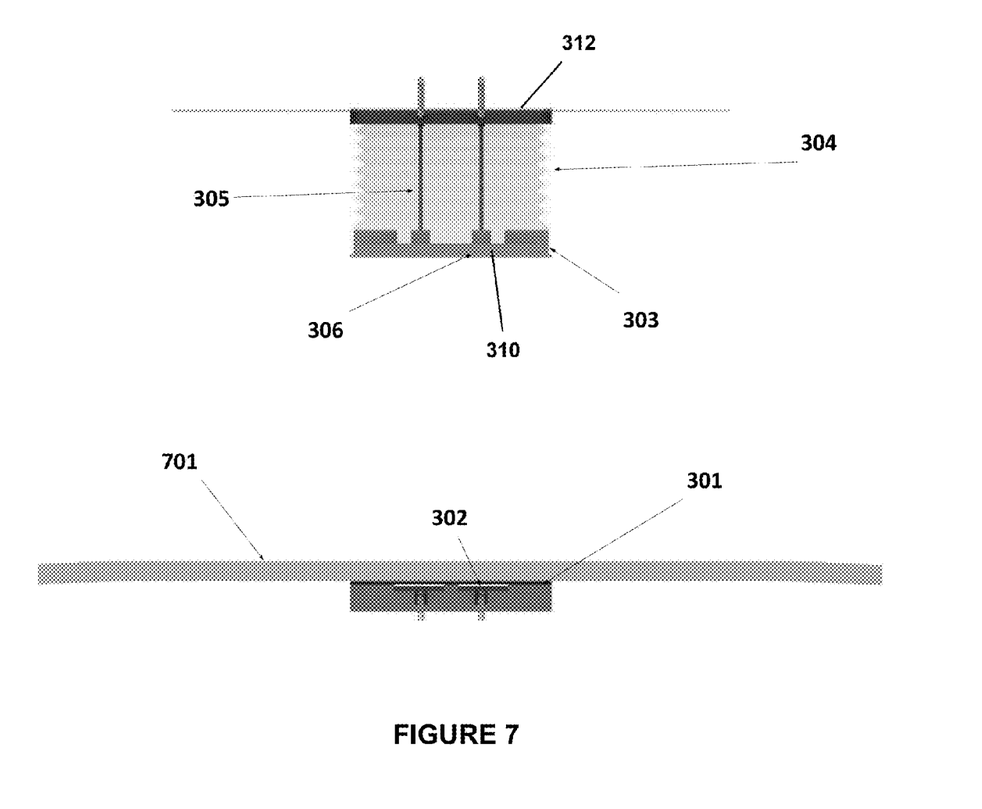
FIG. 7 shows another view of the male and female buttons of FIGS. 1 and 2. The female button 301, located under the skin 701, has female directive inputs 302. The external unit 304 has male pins 305 that use directive holes 306 for alignment as well as "dummy-proof" measures 303.

FIG. 7 shows another embodiment of male unit 304 mating with female unit 301. As described in further detail with respect to FIG. 4, the male unit 304 comprises two structures 310 and 312. The female button 301, located under the skin 701, has female directive inputs 302. First structure 310 is aligned to female button 301 using "dummy-proof" devices 303. First structure 310 additionally has directive holes 306 which will guide prongs 305 into the corresponding female ports 302. Prongs 305 are attached to the second structure 312. Once the first structure 310 is aligned against female unit 301, force against second structure 312 will drive prongs 305 through skin 701 and into the correct female ports 302. Thus an emergency wired connection for power or communication is established.

The invention thus relates to a safety mechanism to be employed when wired power delivery is needed to replace a non-working or otherwise problematic wireless power transfer system. The safety mechanism of the invention also can involve, in addition to wired power delivery, wired control information delivery. As indicated in FIGS. 1 and 2, not only can power be transferred wirelessly into the body of a patient to be received and used by an implanted device, but an external controller unit also can be provided. This external controller can provide control information wirelessly when the wireless transfer system (whether CET or TET) is operating, but, when the external male unit is physically coupled to the implanted female unit such that direct wired power delivery is provided, that male/female unit physical connection also can allow for control information to be provided via the wired direct connection. The control information can include communication such as instructions or settings for the implanted device. The same wire or wires that transfer the power in the wired safety situation can be used to send control information (using, for example, "Power over Ethernet"—PoE, power line communication, or power line carrier—PLC), or else one or more wires can be added and dedicated to communication.

Various modifications may be made to the embodiments disclosed herein. The disclosed embodiments and details should not be construed as limiting but instead as illustrative of some embodiments and of the principles of the invention.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are therefore intended to be embraced therein.

The invention claimed is:

1. A safety apparatus for providing backup power to a wirelessly-powered implantable medical device, the safety apparatus comprising:
    an implantable female unit comprising one or more receiving ports, the implantable female unit being disposable beneath the epidermis of a subject and electrically couplable to and separate from a wirelessly-powered implantable medical device; and
    an external system comprising an external male unit coupled to an external power source, the male unit comprising one or more prongs configured to puncture and be inserted through the epidermis of the subject and received by the one or more receiving ports of the implantable female unit,
    wherein the external system is configured to determine failure of wireless transfer of power to the medical device and, upon the determination of failure, insertion of the one or more prongs of the external male unit through the subject's epidermis and into the one or more ports of the implanted female unit provides a wired connection between the external power source and the medical device, thereby providing external backup power to the medical device.

2. The safety apparatus of claim 1, wherein the wired connection provides transfer of the external backup power and communications between an external controller electrically coupled to the external power source and the medical device.

3. The safety apparatus of claim 1, wherein the safety apparatus is coupled to a coplanar energy transfer (CET) system or a transcutaneous energy transfer (TET) system.

4. The safety apparatus of claim 1, wherein the male and female units are configured such that they can be coupled together in only one physical orientation.

5. The safety apparatus of claim 1, wherein the male and female units comprise magnets.

6. The safety apparatus of claim 4, wherein the male and female units can be coupled together in only one physical orientation due to magnetic repulsion when the male and female units are not in the proper physical orientation.

7. A system for providing backup power to a wirelessly-powered implantable medical device, the system comprising:
   a wirelessly-powered implantable medical device having an implantable receiver electrically coupled thereto and configured to wirelessly receive power transmitted from an external transceiver coupled to an external power source, thereby providing wireless transfer of power to the medical device; and
   a safety mechanism for providing backup power to the medical device upon failure of wireless transfer of power to the medical device, the safety mechanism comprising:
      an implantable female unit comprising one or more receiving ports, the implantable female unit being disposable beneath the epidermis of a subject and electrically coupled to and separate from the wirelessly-powered implantable medical device when the implantable medical device is implanted within the body of the subject; and
      an external system comprising an external male unit coupled to the external power source, the male unit comprising one or more prongs configured to puncture and be inserted through the epidermis of the subject and received by the one or more receiving ports of the implantable female unit,
      wherein the external system is configured to determine failure of wireless transfer of power to the medical device and, upon the determination of failure, insertion of the one or more prongs of the external male unit through the subject's epidermis and into the one or more ports of the implanted female unit provides a wired connection between the external power source and the medical device, thereby providing external backup power to the medical device.

8. The system of claim 7, further comprising an external controller configured to provide control information to the medical device by way of the wireless connection provided by the external transceiver and implanted receiver or the wired connection provided by coupling of the external male unit with implanted female unit.

9. The system of claim 7, wherein the system is coupled to a coplanar energy transfer (CET) system or a transcutaneous energy transfer (TET) system.

10. The system of claim 7, wherein the male and female units are configured such that they can be coupled together in only one physical orientation.

11. The system of claim 7, wherein the male and female units comprise magnets.

12. The system of claim 10, wherein the male and female units can be coupled together in only one physical orientation due to magnetic repulsion when the male and female units are not in the proper physical orientation.

13. A method for providing backup power to a wirelessly-powered implanted medical device within a subject, the method comprising:
   providing a wirelessly-powered medical device implanted within a subject;
   providing a safety mechanism for providing external backup power to the medical device upon failure of wireless transfer of power thereto, the safety mechanism comprising a female unit comprising one or more receiving ports and being disposed beneath the epidermis of the subject and being electrically coupled to the medical device and an external system comprising an external male unit coupled to an external power source, the male unit comprising one or more prongs;
   determining, with the external system, whether wireless transfer of power to the medical device fails;
   puncturing the subject's epidermis with the one or more prongs of the external male unit and inserting the one or more prongs through the subject's epidermis and into the one or more receiving ports of the female unit when failure of wireless transfer of power is determined by the external system, thereby electrically coupling the male and female units to one another and establishing a wired connection between the external power source and the medical device; and
   providing external backup power to the medical device via the wired connection.

14. The method of claim 13, wherein the wired connection additionally provides communication with the medical device.

15. The method of claim 13, wherein the female and male units can only be coupled in one physical orientation.

* * * * *